US011357974B2

(12) United States Patent
Schroeder et al.

(10) Patent No.: US 11,357,974 B2
(45) Date of Patent: Jun. 14, 2022

(54) ELECTRICALLY CONDUCTIVE GEL AND CONDUCTIVE HUMAN INTERFACES AND ELECTRODES FORMED USING ELECTRICALLY CONDUCTIVE GEL

(71) Applicant: WillowWood Global LLC, Mt. Sterling, OH (US)

(72) Inventors: Ryan Schroeder, Westerville, OH (US); Stephen Byers, Dublin, OH (US)

(73) Assignee: WILLOWWOOD GLOBAL LLC, Mt. Sterling, OH (US)

( * ) Notice: Subject to any disclaimer, the term of this patent is extended or adjusted under 35 U.S.C. 154(b) by 1188 days.

(21) Appl. No.: 15/726,624

(22) Filed: Oct. 6, 2017

(65) Prior Publication Data

US 2018/0296822 A1    Oct. 18, 2018

Related U.S. Application Data

(60) Provisional application No. 62/404,936, filed on Oct. 6, 2016.

(51) Int. Cl.

| | | |
|---|---|---|
| *A61F 2/72* | (2006.01) | |
| *A61N 1/04* | (2006.01) | |
| *A61B 5/296* | (2021.01) | |
| *A61F 2/78* | (2006.01) | |
| *A61L 31/12* | (2006.01) | |
| *A61L 31/14* | (2006.01) | |
| *H01B 1/24* | (2006.01) | |
| *H01B 5/14* | (2006.01) | |

(52) U.S. Cl.
CPC ............ *A61N 1/0496* (2013.01); *A61B 5/296* (2021.01); *A61F 2/72* (2013.01); *A61F 2/7812* (2013.01); *A61L 31/126* (2013.01); *A61L 31/14* (2013.01); *A61N 1/0456* (2013.01); *H01B 1/24* (2013.01); *H01B 5/14* (2013.01); *A61B 2562/125* (2013.01); *A61B 2562/14* (2013.01); *A61B 2562/227* (2013.01); *A61F 2002/7818* (2013.01)

(58) Field of Classification Search
CPC .. A61F 2/72; A61F 2/7812; A61F 2002/7818; A61L 31/126; H01B 1/24; A61N 1/0496
See application file for complete search history.

(56) References Cited

U.S. PATENT DOCUMENTS

| | | | |
|---|---|---|---|
| 4,522,211 A | | 6/1985 | Bare |
| 4,898,783 A | | 2/1990 | McCullough, Jr. et al. |
| 5,443,525 A | * | 8/1995 | Laghi ........................ A61F 2/72 |
| | | | 600/384 |
| 5,606,149 A | | 2/1997 | Yaworski et al. |

(Continued)

OTHER PUBLICATIONS

Copending U.S. Appl. No. 15/675,088, filed Aug. 11, 2017, Wernke, et al.

(Continued)

*Primary Examiner* — Bruce E Snow
(74) *Attorney, Agent, or Firm* — Thompson Hine LLP

(57) ABSTRACT

A conductive human interface includes an insulating body of elastomeric material and a compliant electrode embedded in the insulating body. The electrode is formed from an electrically conductive gel including a polymeric material and conductive particles dispersed in the polymeric material. The conductive particles can be included in the gel in an amount that is not more than about 10% by weight.

19 Claims, 8 Drawing Sheets

(56) References Cited

U.S. PATENT DOCUMENTS

| | | |
|---|---|---|
| 6,803,332 B2 | 10/2004 | Andrews |
| 8,123,568 B2 | 2/2012 | Meyer et al. |
| 8,320,988 B2 | 11/2012 | Axelgaard |
| 8,591,599 B1 | 11/2013 | Kaliki et al. |
| 8,948,839 B1 | 2/2015 | Longinotti-Buitoni et al. |
| 8,971,983 B2 | 3/2015 | Gilmore et al. |
| 8,979,944 B2 | 3/2015 | Laghi et al. |
| 9,155,634 B2 | 10/2015 | Lipschutz et al. |
| 9,293,901 B2 | 3/2016 | Lind et al. |
| 2003/0175513 A1 | 9/2003 | Tokarsky et al. |
| 2004/0015222 A1 | 1/2004 | Nielsen |
| 2005/0049481 A1 | 3/2005 | Gray et al. |
| 2005/0184619 A1 | 8/2005 | Chen |
| 2005/0288775 A1 | 12/2005 | Dong |
| 2007/0021841 A1 | 1/2007 | Al-Temen et al. |
| 2007/0078324 A1 | 4/2007 | Wijisiriwardana |
| 2009/0216339 A1 | 8/2009 | Hanson et al. |
| 2010/0114238 A1 | 5/2010 | Muccio |
| 2011/0230747 A1 | 9/2011 | Rogers et al. |
| 2011/0251469 A1 | 10/2011 | Varadan |
| 2012/0035435 A1 | 2/2012 | Choi et al. |
| 2012/0126199 A1 | 5/2012 | O'Brien et al. |
| 2012/0296445 A1* | 11/2012 | Leiniger ............... A61F 2/7812 623/25 |
| 2013/0041235 A1 | 2/2013 | Rogers et al. |
| 2013/0046394 A1 | 2/2013 | Lipschutz |
| 2013/0093287 A1 | 4/2013 | Biso et al. |
| 2013/0248163 A1 | 9/2013 | Bhagwagar et al. |
| 2014/0005763 A1 | 1/2014 | Cederna et al. |
| 2014/0025183 A1* | 1/2014 | Kelley ................. A61F 2/7812 623/36 |
| 2014/0148916 A1 | 5/2014 | Laghi et al. |
| 2015/0087951 A1 | 3/2015 | Felix et al. |
| 2015/0335288 A1 | 11/2015 | Toth et al. |
| 2016/0158034 A1 | 6/2016 | Laghi et al. |
| 2016/0194792 A1 | 7/2016 | Satharasinghe et al. |
| 2018/0296822 A1* | 10/2018 | Schroeder ............ A61L 31/126 |

OTHER PUBLICATIONS

U.S. Patent and Trademark Office, Final Office Action, U.S. Appl. No. 15/675,088, 20 pages, dated Dec. 24, 2021.

U.S. Patent and Trademark Office, Notice of Allowance, U.S. Appl. No. 16/402,555, 9 pages, dated Sep. 3, 2021.

* cited by examiner

ELECTRICALLY CONDUCTIVE GEL AND CONDUCTIVE HUMAN INTERFACES AND ELECTRODES FORMED USING ELECTRICALLY CONDUCTIVE GEL

RELATED APPLICATIONS

This application claims priority of provisional US. Patent application 62/404,936, filed Oct. 6, 2016, which is incorporated by reference.

TECHNICAL FIELD

This technology relates to electrically conductive gel for forming electrodes to communicate signals between a conductive human interface and the skin of a user.

BACKGROUND

A conductive human interface can use electrodes to communicate signals such as, for example, transcutaneous electrical nerve stimulation (TENS) signals, or electromyographic (EMG) signals, with the skin of the user. In some examples the electrodes can be formed from metallic materials. Metallic electrodes can be stiff and rigid compared to human tissue, whereas polymers can be more compliant and elastic, which can be desired when contacting the skin of a user. Polymers are generally non-conductive, but a conductive polymer can be formed by combining a polymer with a conductive material.

SUMMARY

A conductive human interface can include an insulating body of elastomeric material and an electrode embedded in the insulating body. The electrode can be formed of electrically conductive gel including a polymeric material and conductive additive material dispersed in the polymeric material. In a given example, the conductive additive material is included in the electrically conductive gel at not more than about 10% by weight.

In various examples of the interface, the electrically conductive gel can have a bulk DC resistance of about 1000 a-cm or less. The conductive particles can include amalgamated carbon nanotubes less than about 70 um in length. A majority of the conductive particles can be between about 0.030 inches and about 0.050 inches in size. The electrode may have hardness greater than the hardness of the insulating body in which the electrode is embedded. The elasticity of the electrode, as indicated as an Elongation at Break, may be equal or substantially equal to that of the insulating body.

BRIEF DESCRIPTION OF THE DRAWINGS

FIG. 5 is a cross-sectional view along line 5-5 of FIG. 4.

FIG. 8 is a schematic view of a processing device.

DETAILED DESCRIPTION

Figure 1:
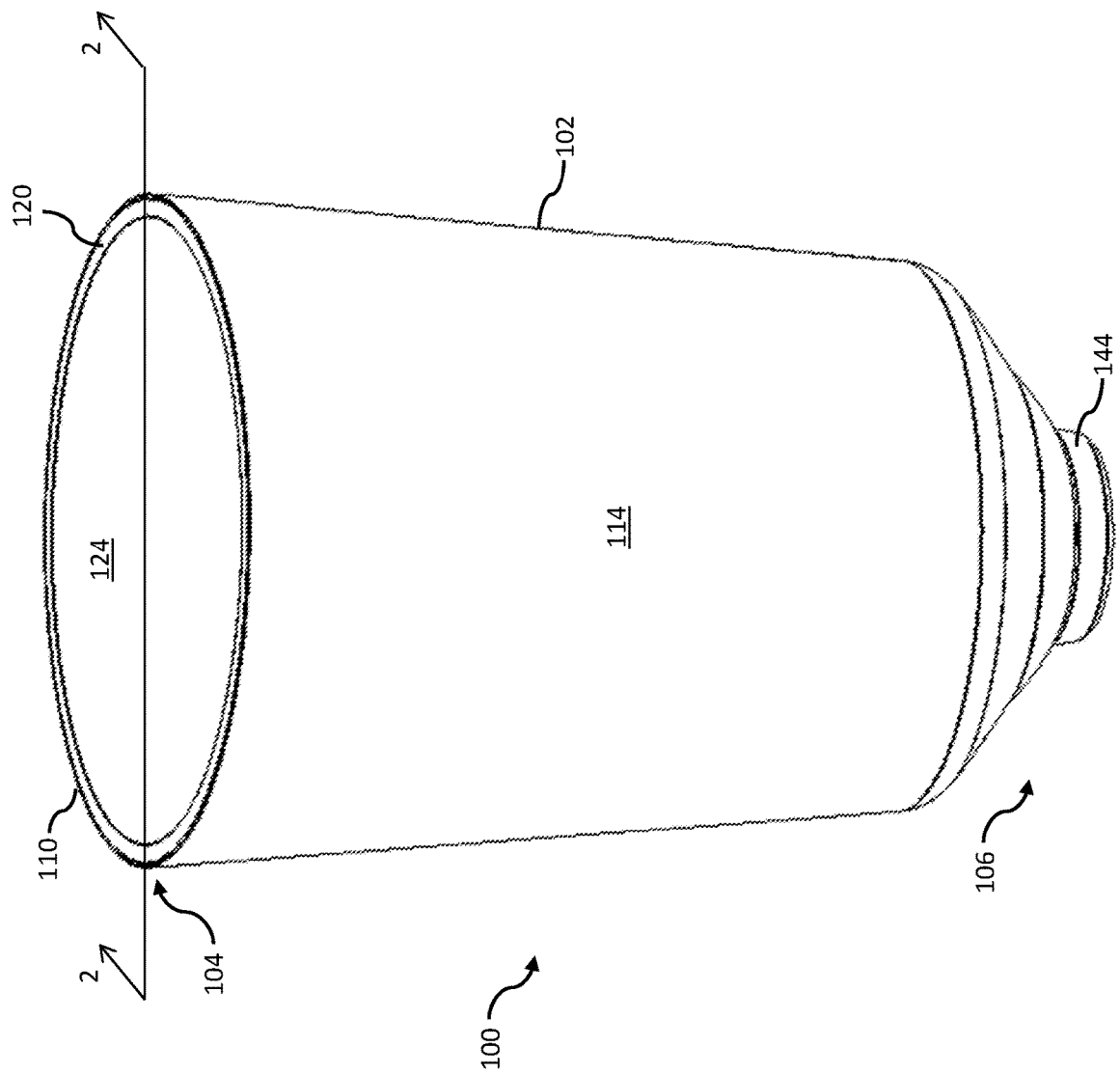
FIG. 1 is a schematic view of a conductive human interface.

The embodiments illustrated in the drawings have parts that are examples of the elements recited in the claims. The illustrated embodiments thus include examples of how a person of ordinary skill in the art can make and use the claimed invention. They are described here to meet the enablement and best mode requirements of the patent statute without imposing limitations that are not recited in the claims. One or more of the elements of one embodiment may be used in combination with, or as a substitute for, one or more elements of another as needed for any particular implementation of the invention.

Figure 2:
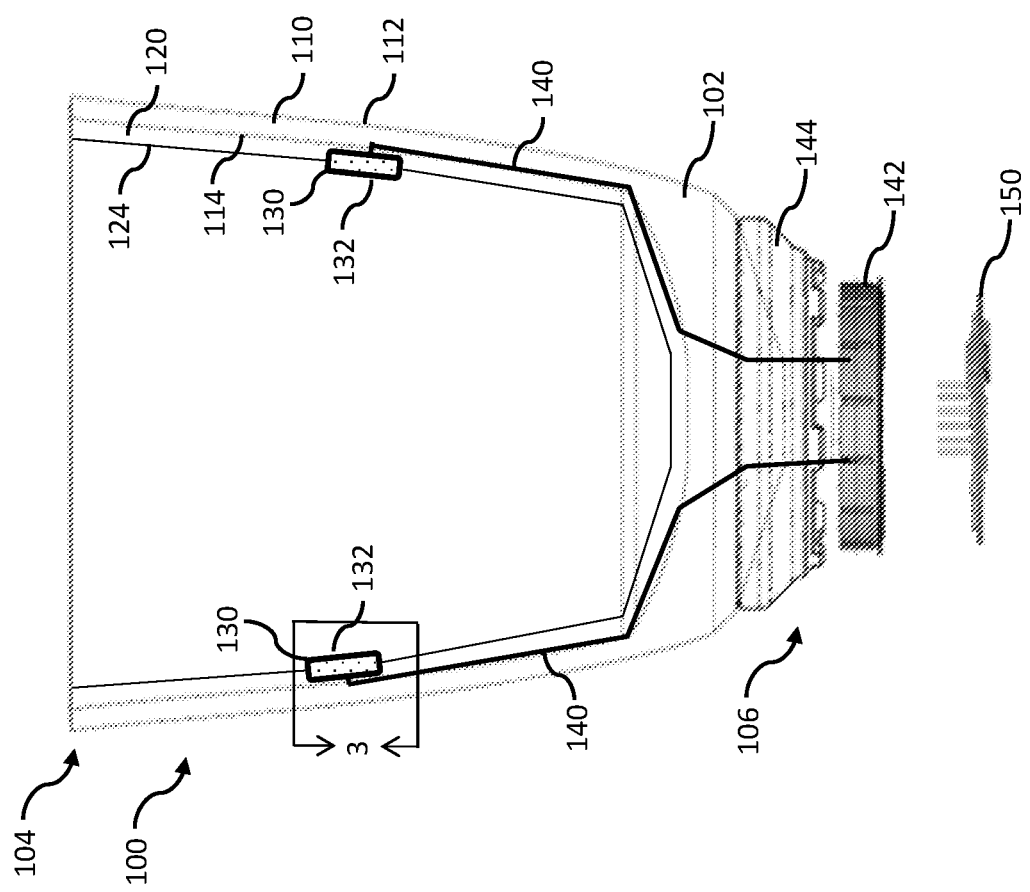
FIG. 2 is an exploded view of an interface system including a partial cross-sectional view of the conductive human interface of FIG. 1 along line 2-2.

An example of a conductive human interface 100 is shown schematically in FIGS. 1 and 2. The conductive human interface 100 is configured to communicate electrical signals with the skin of a user and act as a physical interface with the user. The conductive human interface 100 is also be configured to interface with an assistive device. The assistive device can be any device supplemental to the body of a user that cooperates with the neuromuscular and skeletal system of the user such as, for example, a prosthetic device (e.g., a prosthetic socket), an orthotic device, an exoskeletal device, a powered wheelchair, or the like. Accordingly, while the example of FIG. 1 relates to a prosthetic liner 102, the conductive human interface 100 can alternatively include a sleeve, a band, a pad, or the like.

The conductive human interface 100 includes a fabric layer 110 configured to form a flexible substrate. The fabric layer 110 can include one or more fabric materials such as, for example, stretch controlling fabrics, stretchable nonwoven materials, fiber-on-end fabrics, or the like. Stretch-controlling fabric can be more stretchable in one direction than another direction. For example, a stretch-controlling fabric can have a limited stretch direction that is substantially orthogonal to a non-limited stretch direction. Accordingly, when the conductive human interface 100 includes a prosthetic liner 102, the stretch-controlling fabric can be oriented to permit greater stretch in a circumferential direction than in a longitudinal direction (i.e., along the length of the prosthetic liner 102).

Figure 3:
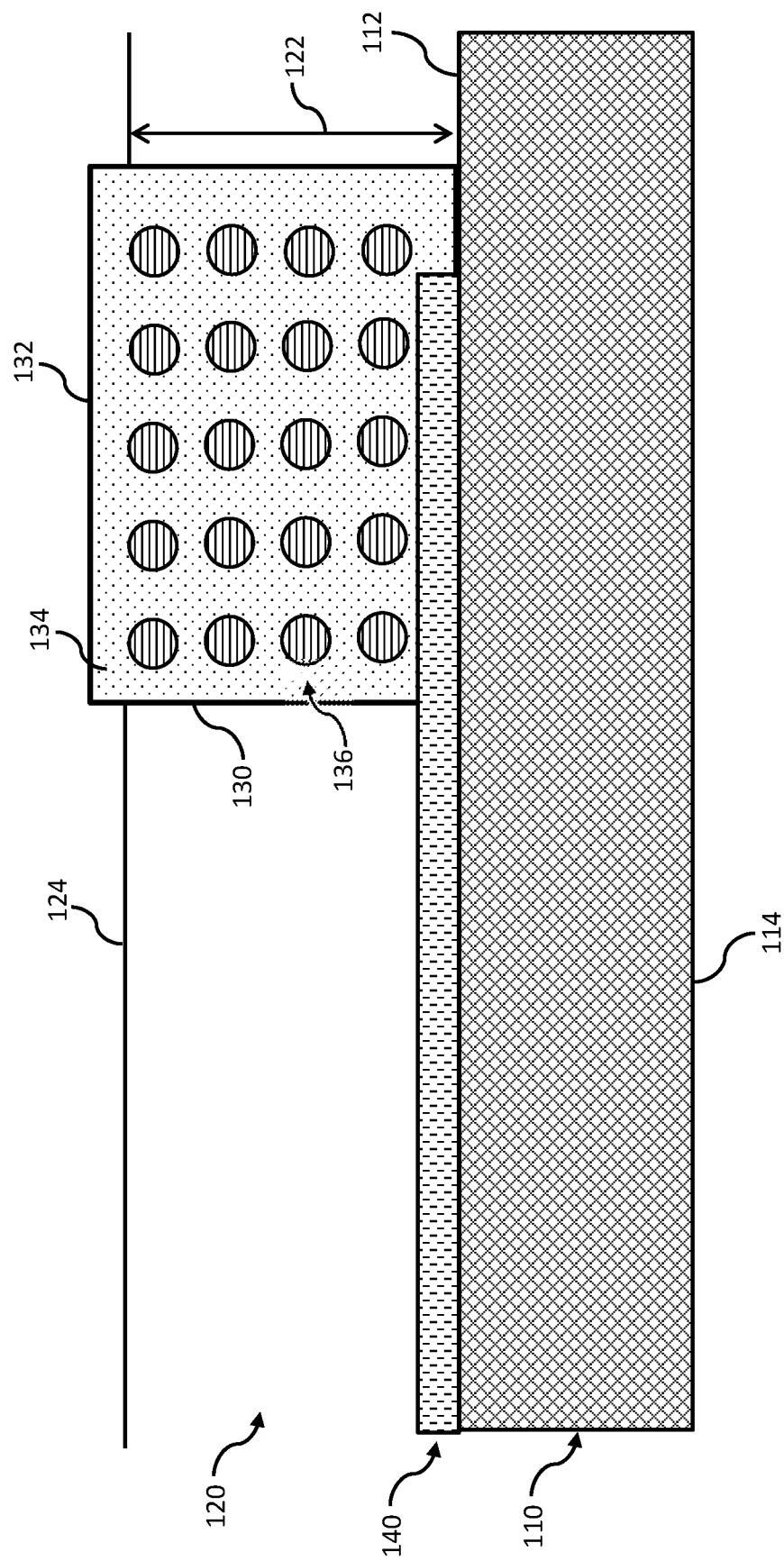
FIG. 3 is an enlarged partial view of the conductive human interface of FIG. 2.

Referring now to FIG. 3, the fabric layer 110 can include an interior surface 112 and an exterior surface 114. The interior surface 112 can form a boundary with an insulating body of elastomeric material configured as a soft coating 120 for comfortable long term wear. As used herein, the term "insulating" can mean that a material can be classified as an electrical insulator, i.e., a material having sufficiently high resistivity to substantially prevent current flow when exposed to operating voltages of the device.

The insulating soft coating 120 can be formed from materials having a hardness on the Shore 00 scale such as, for example, a hardness of less than about 75 on the Shore 00 scale, or a hardness within a range of about 15- to about 35 on the Shore 00 scale. These hardness values have been determined to be comfortable based on clinical feedback during extended 12-hour wear periods for durations of several months. Accordingly, the insulating soft coating 120 can be formed from a soft polymer such as, for example, thermoplastic elastomers (TPE), silicones, block copolymers, urethanes, or the like.

The insulating soft coating 120 is a body of elastomeric material with elasticity that can be characterized according to the Elongation at Break of a modified ASTM standard D412. The Elongation at Break can be within a range of about 150% to about 1,500%. Silicone-based materials tend to be near the lower end of that range, and TPE tends to be near the upper end of that range.

Referring to FIGS. 2 and 3, the conductive human interface 100 can include one or more compliant electrodes 130. The compliant electrodes 130 are configured to make contact with the skin of the user to receive EMG signals produced by muscles of the user, or to transmit electrical signals to the skin of the user. The compliant electrodes 130 are embedded in the insulating soft coating 120, and can either protrude beyond the contact surface 124 of the insulating soft coating 120 be substantially even with the contact surface 124. Each compliant electrode 130 can include a detection surface 132 shaped to promote electrical contact with the skin of the user. For example, the detection surface 132 can be domed shaped, substantially flat, concave shaped, corrugated or any other surface treatment that promotes electrical conductivity with the skin.

Generally, the compliant electrode 130 can be formed from an electrically conductive gel 134. The electrically conductive gel 134 can be formulated such that the compliant electrode 130 has a bulk DC resistance suitable to replace metallic materials while maintaining operability. Titanium electrodes typically have a very low bulk resistivity of about 0.006 a-cm. Applicant has discovered that the compliant electrodes 130 do not need a corresponding low bulk DC resistance. Instead, Applicant has discovered that a bulk DC resistance of up to about 1,000 a-cm can have a reasonably low attenuation of EMG signals and can provide a sufficient signal to noise ratio (SNR) to control a prosthesis. Accordingly, the electrodes 130 can have a bulk DC resistance that is about 1000 a-cm or less, and preferably within a range of about 50 a-cm to about 500 a-cm. Acceptable bulk contact DC resistance is dependent upon the input impedance of the instrumentation used to monitor the electromyographic signals and these ranges were complementary to modern instrumentation amplifiers.

The electrically conductive gel 134 can be formed from a polymeric material that is compounded with a conductive additive 136. The polymeric material can include TPE, silicones, block copolymers, urethanes, or the like. In some embodiments, the polymeric material of the electrically conductive gel 134 can comprise a medical grade silicone such as, for example, Dragon Skin® 30 silicone by Smooth-On, Inc. of Macungie, Pa., USA.

The polymeric material of the electrically conductive gel 134 can be selected based upon elasticity. Like the insulating soft coating 120, the compliant electrode 130 is a body of elastomeric material with elasticity that can be characterized according to the Elongation at Break of a modified ASTM standard D412. The Elongation at Break of the gel 134 at each electrode 130 is preferably equal or substantially equal to the elongation at break of the soft coating 120. Alternatively or additionally, the Elongation at Break of the polymeric material of the electrically conductive gel 134 can be within a range of about 50% to about 200%. These values of elongation are compatible with existing prosthetic liner elongation ranges, so there is not a large mechanical concentration of stress that might otherwise occur between the electrodes 130 and the coating 120 when the liners are stretched. Such a concentration of stress has been shown to lead to premature failure and delamination of the contact interface. Accordingly, the compliant electrode 130 can be configured to conform and flex with the skin of the user as both move during use.

The conductive additive 136 can comprise conductive materials such as, for example, gold, copper, nickel, iron, iron-oxide, silver, carbon, carbon black, carbon nanotubes, graphite, or combinations thereof. The conductive additives 136 can be provided as conductive particles, conductive strands, or both. The conductive particles can correspond to various shapes such as, but not limited to, spherical, rounded, angular, spongy, flakey, cylindrical, acicular, cubic, or the like. For example, in some embodiments, the conductive particles can be formed from amalgamated carbon nanotubes such as, for example, macro particle flakes. Suitable amalgamated carbon nanotubes include Carbon NanoStructures (CNS), which can be formed as a cross-linked and entangled arrangement of carbon nanotubes on a base material, provided by Applied NanoStructured Solutions, LLC of Baltimore, Md., USA. The cross-linked and entangled carbon nanotube within the conductive particles can have an average length of about 70 um (+/−about 20 um) with a rough thickness of about 10 um. If the particles are excessively long, they can protrude from the material surface and irritate the skin.

Generally, the size of the conductive particles can be controlled by screening the particles through an orifice having a known dimension. The majority of the conductive particles can have a size less than about 0.075 inches (about 1.9 mm). The size may be within a range of about 0.030 inches (0.76 mm) to about 0.050 (about 1.27 mm) inches, such as a size of about 0.040 inches (about 1 mm). Another suitable range could extend from about 0.002 inches (about 50 um) to about 0.040 inches (about 1 mm). These lengths of particles were found to not significantly protrude from the surface of the interface did not result in skin irritation during clinical evaluation.

The conductive strands can be formed from one or more conductive filaments that are spun or twisted together into a substantially cord-like shape. For example, the conductive filaments can include an insulating substrate, which can be coated or embedded with electrically conductive elements such as, for example, silver, carbon, nickel, copper, gold, titanium, or the like. Substrates can include cotton, polyester, nylon, aramids, or the like. The diameter of the conductive strands can be less than about 0.006 inches (about 0.15 mm) such as, for example, less than about 0.002 inches (about 0.05 mm). The conductive additive 136 can also comprise conductive strands having different diameters. Alternatively or additionally, the conductive additive 136 can comprise conductive strands having different coatings, substrates, or both. The length of the conductive strands can be less than about 0.2 inches (about 5 mm), such as for example, within a range of about 0.12 inches (about 3 mm) to about 0.16 inches (about 4 mm). The detection surface 132, or the entirety of the compliant electrode 130, can be formed from electrically conductive gel 134 having conductive particles without the use of conductive strands.

Referring still to FIGS. 2 and 3, the amount of the conductive additive 136 can be controlled as a weight percentage of the electrically conductive gel 134. The weight percentage of the conductive additive 136 can impact the electrical and mechanical characteristics of the compliant electrodes 130. If too few conductive particles are included, the gel will have bulk conductivity that is too low to conduct signals sufficiently to the receiving electronics. If the concentration of conductive particles is too high, the gel will have a low tear strength which clinical testing has shown is undesirable. Additionally, if the percentage of conductive additive is too high, the uncured material can crumble, which makes molding difficult, or can coagulate, which makes even mixing difficult.

In embodiments where the conductive additive 136 comprises conductive particles, the conductive particles can be dispersed throughout the electrically conductive gel 134. The conductive particles are preferably included in the electrically conductive gel 134 in an amount not more than about 10% by weight. The conductive additive 136 can thus be included in the electrically conductive gel 134 within a range of about 1% to about 10% by weight.

The electrically conductive gel 134 can be provided as a moldable material, i.e., the viscosity of the material can be controlled. In some embodiments, the viscosity of the electrically conductive gel 134, in an uncured state and compounded state, can be less than about 20 million cP such as, for example, within a range of about 1 million cP to about 10 million cP. Applicants discovered that compounding too much of the conductive additive 136 in the electrically conductive gel 134 can render the electrically conductive gel 134 difficult to mold, i.e., increase the difficulty of forming the compliant electrode 130. Specifically, the electrically conductive gel 136 can congeal into a plurality of clumps or form into a powder having an undesirably high viscosity. It is noted that viscosity can be determined using a Rubber Process Analyzer such as the D-RPA 300 available from MonTech Inc. of Columbia City, Ind., USA.

Once cured the electrically conductive gel 134, and thus the compliant electrode 130, can be configured to maintain comfortable contact with the skin of the user for an entire day (e.g., about 18 hours). Accordingly, the hardness, the elasticity, or both of the electrically conductive gel 134 and the compliant electrode 130 can be controlled. In some embodiments, the hardness of the compliant electrode 130 can be greater than the hardness of the insulating soft coating 120. This can promote contact with the skin of the user. In other words, lift off can be mitigated by providing the compliant electrode 130 with greater hardness than the insulating soft coating 120, which can increase contact pressure between the compliant electrode 130 and the skin of the user. The compliant electrode 130 can thus have a hardness on the Shore 00 scale of up to about 100.

Referring to FIGS. 2 and 3, the conductive human interface 100 can include a conductive path 140 for electrically connecting each of the one or more compliant electrodes 130 to assistive device or another component. As used herein, the phrase "electrically connect" can mean to provide a medium for the transmission of electrical signals from one object to another object. The conductive path 140 generally includes a flexible conductor such as, for example, conductive thread, conductive fabric, conductive ink, or combinations thereof. It has been discovered that wires may be unsuitable for use with certain embodiments of the conductive human interface 100. For example, wires can include conductors or shielding that can be substantially more rigid than the fabric layer 110, the insulating soft coating 120, or both. The difference in rigidity can damage the insulating soft coating 120 and reduce the durability of the conductive human interface 100 and cause discomfort. Additionally, the difference in rigidity can cause the wires to fatigue and lose conductivity.

In some embodiments, the compliant electrode 130 can be molded over the conductive path 140. For example, the compliant electrode 130 can be applied directly to the conductive path 140. Accordingly, the compliant electrodes 130 can make surface contact with the conductive path 140 or both the conductive path 140 and the interior surface 112 of the fabric layer 110. In some embodiments, the electrically conductive gel 134 can be applied directly to the conductive path 140 in an uncured state and cured to form the compliant electrode 130. In some embodiments, the electrically conductive gel 134 can be applied before the insulating soft coating 120 is applied. Alternatively, the electrically conductive gel 134 of the compliant electrodes 130 or the compliant electrodes 130 can be applied after the insulating soft coating 120 is applied. For example, a removable body can cover the compliant electrode sites on the conductive path 140, while the insulating soft coating 120 is applied. The removable body can then be removed to allow the compliant electrodes 130 to be applied to the compliant electrode sites. Alternatively or additionally, the compliant electrode 130 can be connected to the conductive path via a connector. For example, the connector can be formed from conductive materials such as, for example, a metal (e.g., copper, aluminum, gold, silver, etc.) or a graphite material.

The conductive human interface 100 can include an electrical connector 142 configured to electrically connect each conductive path 140 with an assistive device as described above, or with another component. The electrical connector 142 can include conductive members, each configured to be electrically connected to one of the conductive paths 140. In some embodiments, the electrical connector 142 can be configured to transition from relatively flexible conductors to more rigid conductors. For example, the electrical connector 142 can include a separable electrical connector (e.g., pins, sockets, etc.) electrically connected to the conductive members.

Referring to FIGS. 1 and 2, in some embodiments, the conductive human interface 100 can include the prosthetic liner 102. The prosthetic liner 102 can include an umbrella 144 formed at the closed end 106 and external to the exterior surface 114 of the fabric layer 110. In some embodiments, the umbrella 144 can be formed around the electrical connector 142. For example, the umbrella 144 can be molded to the exterior surface 114 of the fabric layer 110 out of relatively hard materials such as, for example, a hard urethane.

Figure 4:
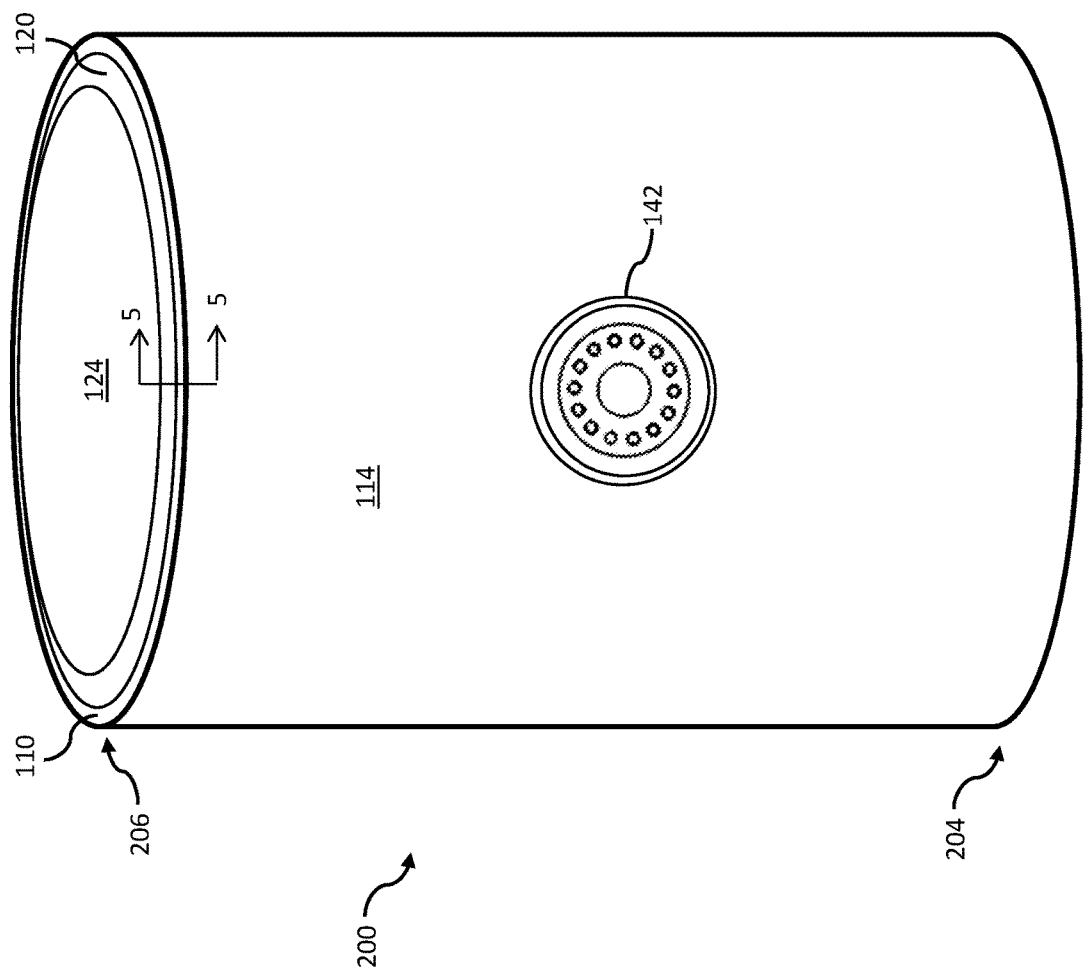
FIG. 4 is a schematic view of an alternative embodiment of a conductive human interface.
Figure 5:
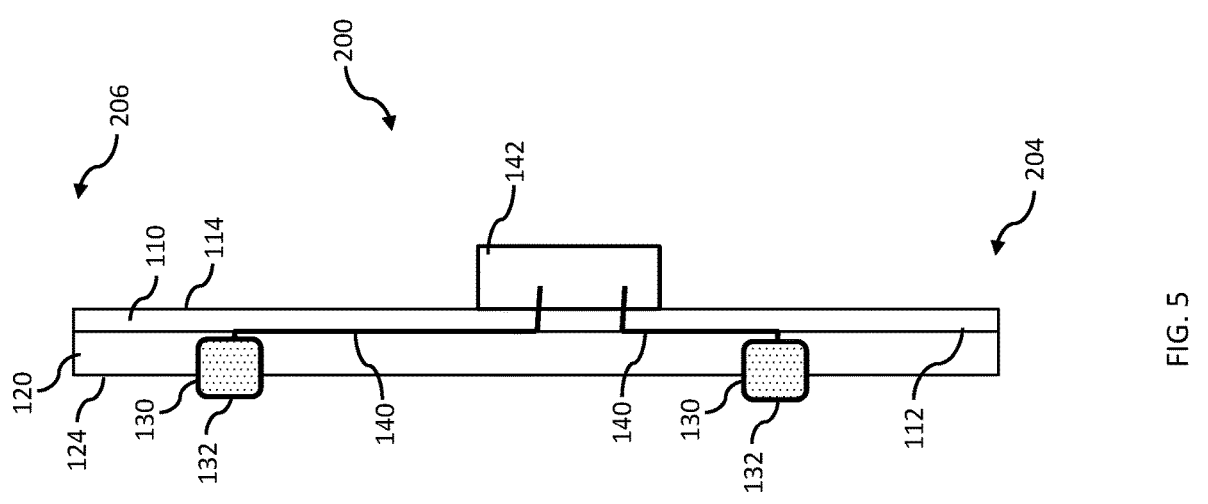

Referring to FIGS. 4 and 5, an embodiment of a conductive human interface 200 can be substantially tubular. For example, the conductive human interface 200 can extend between a first open end 204 and a second open end 206. Accordingly, the conductive human interface 200 can be provided as, for example, an arm sleeve, a leg sleeve, a wrist band, a head band, or the like. Generally, the conductive human interface 200 can include the fabric layer 110, the insulating soft coating 120, the compliant electrode 130, and the electrical connector 142, as described herein with respect to the conductive human interface 100. Additionally, the conductive human interface 200 can be formed in substantially the same way as the conductive human interface 100. In some embodiments, the electrical connector 142 can be provided on the exterior surface 114 of the fabric layer 110 between the first open end 204 and the second open end 206. Alternatively, the electrical connector 142 can be provided at the first open end 204, the second open end 206, or both.

Figure 6:
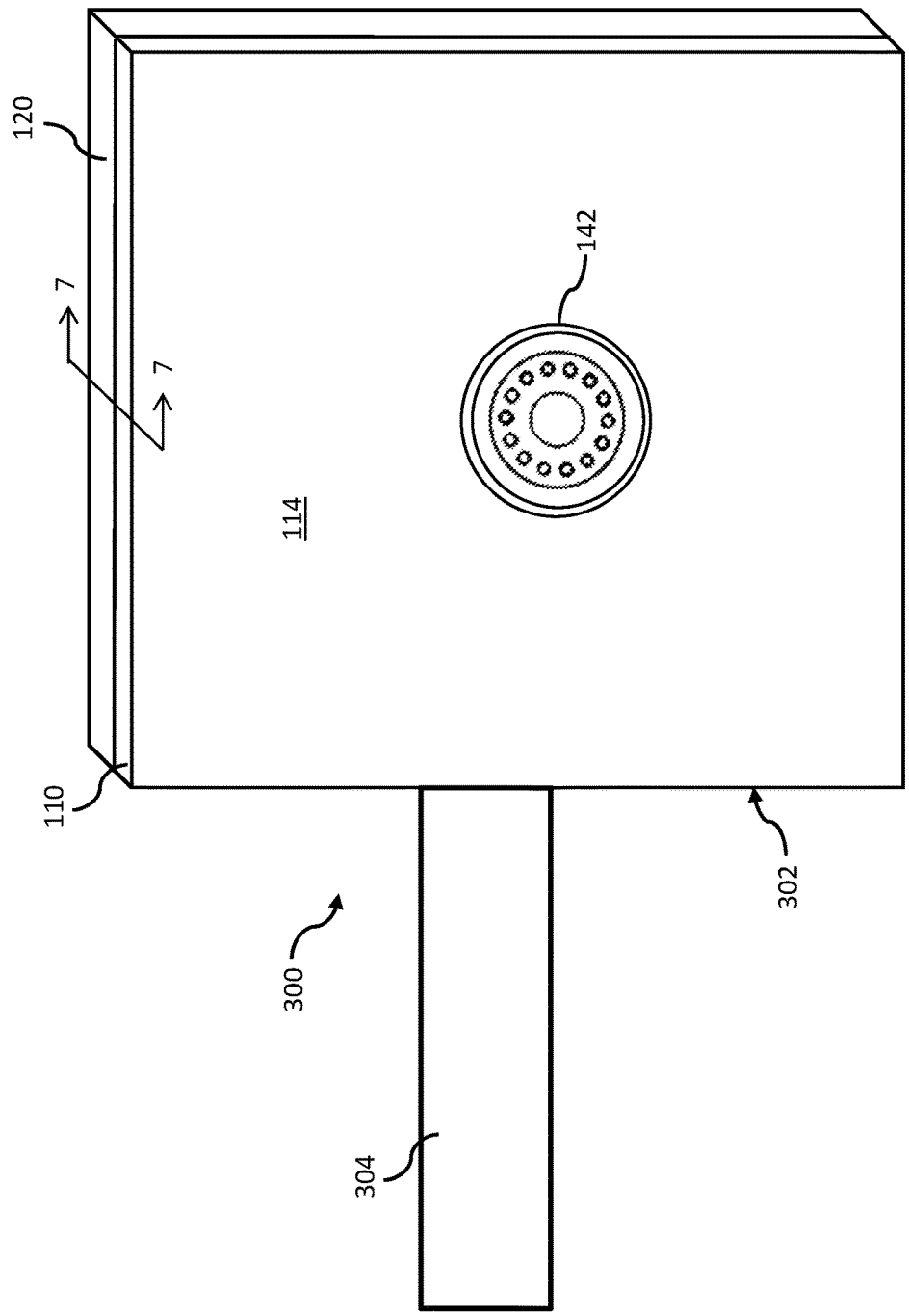
FIG. 6 is a schematic view of another alternative embodiment of a conductive human interface.
Figure 7:
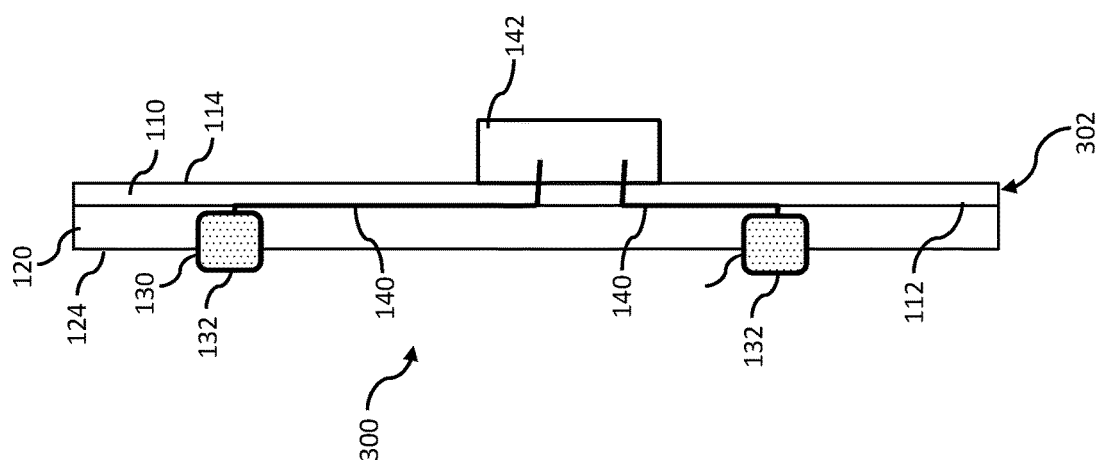
FIG. 7 is a cross-sectional view along line 7-7 of FIG. 6.

Referring to FIGS. 6 and 7, an embodiment of a conductive human interface 300 can be formed as a substantially sheet shaped body. For example, the conductive human interface 300 can have a thickness that is defined by the fabric layer 110 and the insulating soft coating 120 and demarcated by a perimeter 302. It is noted that, while the perimeter 302 is depicted in FIG. 6 as being substantially rectangular, the perimeter can be contoured to match with any desired body part. Optionally, the conductive human interface 300 can include a band 304 configured to wrap around a user and secure the conductive human interface 300 to the desired body part. Generally, the conductive human interface 300 can include the fabric layer 110, the insulating soft coating 120, the compliant electrode 130, and the electrical connector 142, as described herein with respect to the conductive human interface 100. In some embodiments, the electrical connector 142 can be provided on the exterior surface 114 of the fabric layer 110. Additionally, the conductive human interface 300 can be formed in substantially the same way as the conductive human interface 100.

Figure 8:
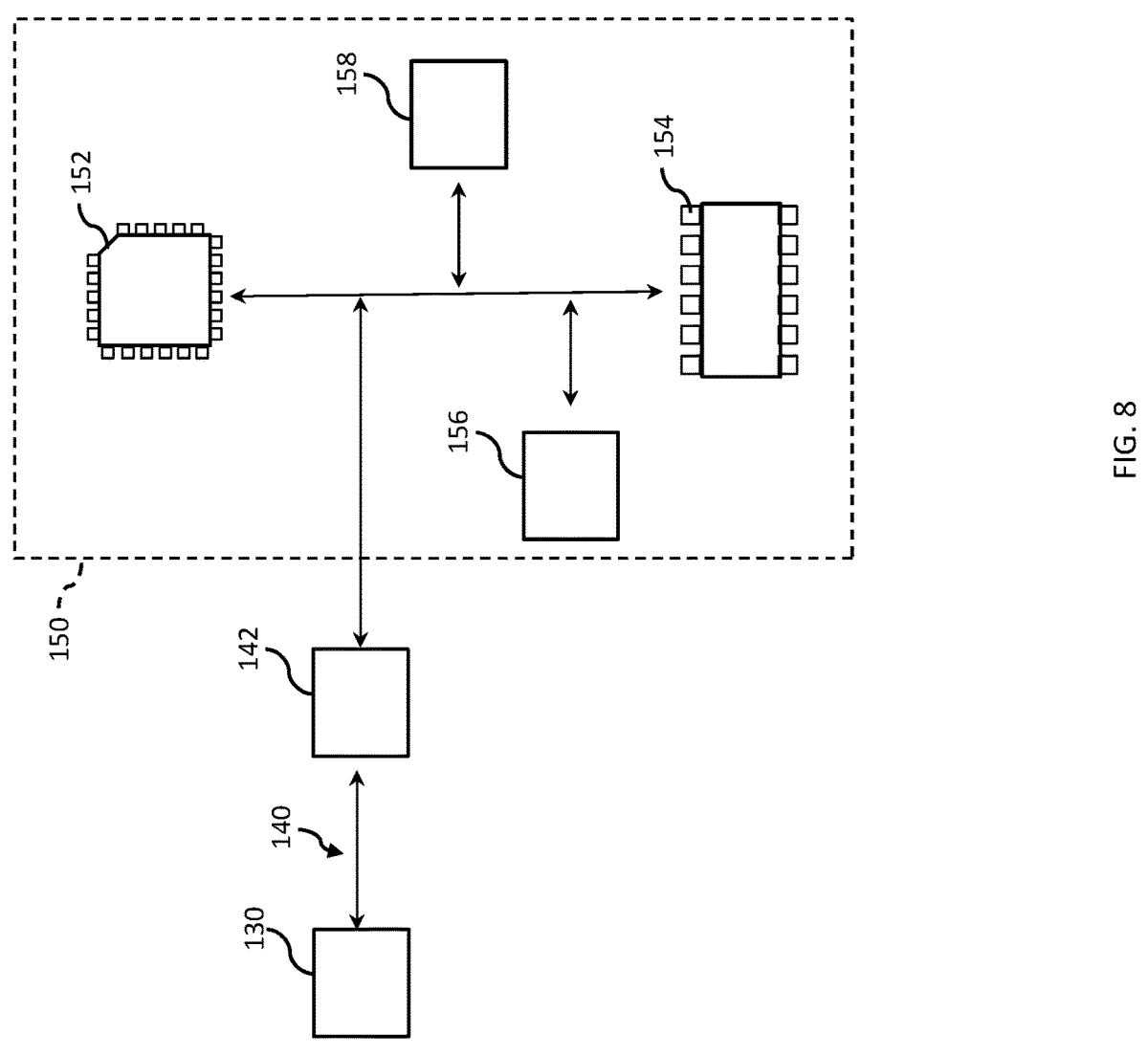

Referring to FIGS. 1, 2, and 8, a processing device 150 can be operable to communicate electrical signals with the one or more compliant electrode 130. The processing board 150 can include one or more processors 152 for executing machine readable instructions to perform signal communication functions, as described herein. The term "processor" can mean any device capable of executing machine readable instructions. Accordingly, each processor can be a controller, an integrated circuit, a microchip, a signal processor, or any other device capable of implementing logic. The processing device 150 can include memory 154 communicatively coupled to the one or more processors 190 (generally depicted as double arrowed lines). As used herein, the phrase "communicatively coupled" can mean that components are capable of exchanging data signals with one another such as, for example, electrical signals via conductive medium, electromagnetic signals via air, optical signals via optical waveguides, and the like. The memory 154 described herein may be RAM, ROM, a flash memory, a hard drive, or any device capable of storing machine readable instructions.

Additionally, it is noted that the functions described herein can be provided as machine readable instructions stored on the memory 154 and executed by the one or more processors 152. The machine readable instructions can be provided in any programming language of any generation (e.g., 1GL, 2GL, 3GL, 4GL, or 5GL) such as, e.g., machine language that may be directly executed by the processor, or assembly language, object-oriented programming (OOP), scripting languages, microcode, etc., that may be compiled or assembled into machine readable instructions and stored on a machine readable medium. Alternatively, the functions, modules, and processes described herein may be written in a hardware description language (HDL), such as logic implemented via either a field-programmable gate array (FPGA) configuration or an application-specific integrated circuit (ASIC), and their equivalents. Accordingly, the functions described herein may be implemented in any conventional computer programming language, as pre-programmed hardware elements, or as a combination of hardware and software components.

The processing device 150 can be configured to transform EMG signals detected by the compliant electrode 130 into control signals for an assistive device. For example, the EMG signals can be conducted from the detection surface 132 of the compliant electrodes 130 to the conductive path 140 and the processing device 150. In some embodiments, the compliant electrodes 130 can be electrically connected to high impedance differential instrument amplifiers of the processing device 150. For example, the one or more compliant electrodes 130 can have a positive contact and a negative contact. The processing device 150 can use the differential amplifier configuration to subtract common electrical noise created from the ambient environment and in electrical line oscillations from the EMG signal. Accordingly, in some embodiments, the positive and negative contacts of the one or more compliant electrodes 130 can have substantially similar bulk DC resistance values, i.e., matched bulk DC resistance values. The differential signal can then be processed for use in controlling an assistive device.

Alternatively or additionally, the processing device 150 can include device communication hardware 156 communicatively coupled to the one or more processors 152. The device communication hardware 156 can be configured to communicate, i.e., send and/or receive data signals via any wired or wireless communication protocol such as, for example, LIN bus, CAN bus, USB, FIREWIRE, IrDA, BLUETOOTH, Wireless USB, Z-WAVE, ZIGBEE, or the like. Accordingly, the one or more processors 152 can receive signals via the electrical connector 142 and transform the signals into control signals. The control signals can then be transmitted via the device communication hardware 194 to the assistive device.

Additionally, the processing device 150 can be configured to transmit electrical signals to the compliant electrode 130. For example, the electrical signals can be configured to stimulate nerve endings, create information flowing into the body, or both. In some embodiments, the processing device 150 can include a signal generator 158 configured to generate electrical signals that can be communicated to the compliant electrode 130. For example, the signal generator 158 can be communicatively coupled to the electrical connector 142 and the one or more processors 152. Accordingly, the one or more processors 152 can cause the signal generator 158 to generate the desired electrical signal. The electrical signal can be transmitted to the compliant electrode 130 via the conductive path 140 and the electrical connector 142. Alternatively, the electrical signals can be provided directly to the electrical connector 142 via the device communication hardware 156. Accordingly, in some embodiments, the signal generator 158 is omitted.

The electrical signals can configured for TENS. Thus, the compliant electrode 130 can be aligned with the desired nerve ending to manage pain. For example, amputees can experience phantom limb pain, i.e., pain that is sensed as coming from an amputated limb. For example, nerve endings at the site of amputation can stimulate the brain in a manner that is interpreted as pain from the removed limb. Alternatively or additionally, the electrical signals can be transmitted to muscle or nerve endings as feedback from an assistive device. For example, amputees using assistive devices such as, for example, a prosthetic foot may have difficulty detecting uneven surfaces. Often times, the amputee may need to look directly at the assistive device in order to traverse an uneven surface. In some embodiments, the assistive device can be provided with sensors configured to detect the uneven surface such as, for example, load sensors to detect the amount and type of loading, and contact sensors configured to detect contact with the surface. In some embodiments, the sensor information can be communicated to the compliant electrode 130 as feedback that can stimulate the brain. For example, the one or more processors 152 can receive sensor data and cause the signal generator 158 to generate the desired electrical signal. The one or more processors 152 can encode the electrical signal according to the sensor data. Alternatively, the electrical signals can be provided directly to the electrical connector 142 via the device communication hardware 158.

Test Example

An electrically conductive gel was formed using Dragon Skin® 30 silicone as the polymeric material, and CNS particles as the conductive additive. The CNS particles were ground into a size less than or equal to about 0.040 inches (about 1 mm). The electrically conductive gel was compounded with about 5% by weight of the CNS particles. The compounded material exhibited suitable viscosity. Various comparative examples were compounded using weight percentage of conductive additives larger than the embodiments provided above. Some of the comparative examples exhibited poor manufacturability, i.e., coagulation, powdering, or inability of the silicone to cure. Once the test example cured, the electrically conductive gel exhibited suitable mechanical properties, as described above, and bulk DC resistance values between about 50 a-cm and about 200 a-cm. Some of the comparative examples exhibited poor mechanical properties such as, for example, low tear strength, crumbling, and biological incompatibility.

This written description sets for the best mode of carrying out the invention, and describes the invention so as to enable a person of ordinary skill in the art to make and use the invention, by presenting examples of the elements recited in the claims. The detailed descriptions of those elements do not impose limitations that are not recited in the claims, either literally or under the doctrine of equivalents.

What is claimed is:

1. A conductive human interface, comprising:
    an insulating body of elastomeric material having a contact surface configured to contact the skin of a user;
    an electrode embedded in the insulating body, wherein the electrode is formed of electrically conductive gel, the electrically conductive gel comprises a polymeric material and conductive additive material dispersed in the polymeric material, and the conductive additive material is included in the electrically conductive gel at not more than about 10% by weight; and
    a fabric layer having an interior surface and an exterior surface, wherein the insulating body and the electrode are applied to the interior surface of the fabric layer.

2. The conductive human interface of claim 1, wherein the electrode has a bulk DC resistance of about 1000 ohms-cm or less.

3. The conductive human interface of claim 1, wherein
    the conductive additive material comprises conductive particles,
    the conductive particles forming between about 1% and about 10% of the electrically conductive gel by weight,
    a majority of the conductive particles are between about 0.030 inches and about 0.050 inches in size;
    an Elongation at Break of the electrically conductive gel is between about 50% and about 200%, and
    the electrically conductive gel has a bulk DC resistance of less than 500Ω.

4. The conductive human interface of claim 3, wherein the electrically conductive gel has a viscosity between about 1 million cP and about 10 million cP, when the electrically conductive gel is in an uncured and compounded state.

5. The conductive human interface of claim 1, wherein the conductive additive material comprises conductive particles.

6. The conductive human interface of claim 5, wherein the conductive particles are within a range of about 1% to about 10% of the electrically conductive gel by weight.

7. The conductive human interface of claim 5, wherein the conductive particles amalgamated carbon nanotubes.

8. The conductive human interface of claim 5, wherein a majority of the conductive particles are less than about 0.075 inches in length.

9. The conductive human interface of claim 1, wherein the electrode has a bulk DC resistance within a range of about 50 ohms-cm to about 500 ohms-cm.

10. The conductive human interface of claim 1, wherein the conductive additive material comprises conductive strands.

11. The conductive human interface of claim 1, wherein the electrode has a hardness greater than a hardness of the insulating body.

12. The conductive human interface of claim 1, wherein the electrode has an Elongation at Break equal or substantially equal to an Elongation at Break of the insulating body.

13. The conductive human interface of claim 1, wherein the electrode has an Elongation at Break within a range of about 50% to about 200%.

14. The conductive human interface of claim 1, further comprising:
    a conductive path electrically connected to the electrode; and
    an electrical connector electrically connected to the conductive path.

15. A conductive human interface, comprising:
    an insulating body of elastomeric material; and
    an electrode embedded in the insulating body, wherein:
        the electrode is formed of electrically conductive gel,
        the electrically conductive gel comprises a polymer and amalgamated carbon nanotubes dispersed in the polymer, and
        the amalgamated carbon nanotubes have an average length not greater than about 70 μm.

16. The conductive human interface of claim 15, wherein the amalgamated carbon nanotubes are within a range of 1% to 7% of the electrically conductive gel by weight.

17. The conductive human interface of claim 15, wherein the electrode has resistance of 1000 ohms-cm or less.

18. The conductive human interface of claim 15, wherein the electrode has a hardness greater than a hardness of the insulating body.

19. The conductive human interface of claim 15, wherein the electrode has an Elongation at Break equal or substantially equal to an Elongation at Break of the insulating body.

* * * * *

UNITED STATES PATENT AND TRADEMARK OFFICE
CERTIFICATE OF CORRECTION

| | |
|---|---|
| PATENT NO. | : 11,357,974 B2 |
| APPLICATION NO. | : 15/726624 |
| DATED | : June 14, 2022 |
| INVENTOR(S) | : Ryan Schroeder and Stephen Byers |

Page 1 of 1

It is certified that error appears in the above-identified patent and that said Letters Patent is hereby corrected as shown below:

In the Claims

Claim 2, Column 9, Lines 39-41 reads:
"2. The conductive human interface of claim 1, wherein the electrode has a bulk DC resistance of about 1000 ohms-cm or less."
Should read:
-- 2. The conductive human interface of claim 1, wherein the electrode has a bulk DC resistance of 1000 ohms-cm or less. --

Signed and Sealed this
Sixth Day of September, 2022

Katherine Kelly Vidal
*Director of the United States Patent and Trademark Office*